(12) United States Patent
Auer et al.

(10) Patent No.: US 7,754,448 B2
(45) Date of Patent: Jul. 13, 2010

(54) METHOD FOR THE RECOMBINANT EXPRESSION OF AN N-TERMINAL FRAGMENT OF HEPATOCYTE GROWTH FACTOR

(75) Inventors: Johannes Auer, Schwaigen (DE); Apollon Papadimitriou, Bichl (DE); Christian Schantz, Munich (DE); Stefan Seeber, Penzberg (DE)

(73) Assignee: Hoffman-La Roche Inc., Nutley, NJ (US)

( * ) Notice: Subject to any disclaimer, the term of this patent is extended or adjusted under 35 U.S.C. 154(b) by 27 days.

(21) Appl. No.: 10/591,045

(22) PCT Filed: Mar. 2, 2005

(86) PCT No.: PCT/EP2005/002176

§ 371 (c)(1),
(2), (4) Date: Aug. 29, 2006

(87) PCT Pub. No.: WO2005/095611

PCT Pub. Date: Oct. 13, 2005

(65) Prior Publication Data

US 2007/0154985 A1 Jul. 5, 2007

(30) Foreign Application Priority Data

Mar. 3, 2004 (EP) .................................. 04004951

(51) Int. Cl.
*C12P 21/06* (2006.01)
*C12N 1/20* (2006.01)
*C12N 15/00* (2006.01)
*C07H 21/04* (2006.01)

(52) U.S. Cl. ................. 435/69.1; 435/320.1; 435/252.3; 435/252.33; 536/23.5

(58) Field of Classification Search ........................ None
See application file for complete search history.

(56) References Cited

FOREIGN PATENT DOCUMENTS

| EP | 0 373 365 | 6/1990 |
|---|---|---|
| EP | 1 234 583 | 8/2002 |
| EP | 1 354 891 | 10/2003 |
| WO | WO 93/23541 | 11/1993 |

OTHER PUBLICATIONS

Stahl et al, "*Biochem Jour*", 326: 763-772 (1997).
Fuglsang A., *Gene An International Journal on Genes and Genomes*, vol. 320, 185-190 (Nov. 2003).
Olivares-Trejo J, et al, *Molecular Microbiology*, 49:4 1043-1049 (Aug. 2003).
Jeh, H. S. et al, *Jour. of Biotechnology*, 60:3 1831-93 (Feb. 1998).
Date K et al, *FEBS Letters*, 420:1 1-6 (1997).
Date, K. et al, *Oncogene 17*, (1989) 3045-3054.
Albini, A. et al, *Cancer Res.*, 47 3239-3245 (1987).
Chan, A. M. et al, *Science*, 254 1382-1385 (1991).
Kuba, K. et al, *Cancer Res*, 60 6737-6743 (2000).
Lokker, N. A. et al, *Biol. Chem.* 268 17145-17150 (1993).
Lokker, N. A., *EMBO J.*, 11 2503-2510 (1992).
Miyazawa, K. et al, *Biochem.Biophy. Res. Comm*, 163 967-973 (1989).
Nakamura, T. et al, *Biochem. Biophys. Res. Comm*, 122 1450-1459 (1984).
Okajima, A. et al, *Eur. J. Biochem.* 193 375-381 (1990).
Parr, C. et al, *Int. J. Cancer*, 85 563-570 (2000).
Seki, T. et al, *Biochem. and Biophys. Res. Comm*, 172 321-327 (1990).
Stuart, K.A. et al, *Int. J. Exp. Pathol.*, 81 17-30 (2000).
Tashiro, K. et al, *Proc. Natl. Acad. Sci.* 87 3200-3204 (1990).
Weidner, K.M. et al, *Proc. Natl. Acad. Sci*, 88 7001-7005 (1991).
Nakamura, T. et al, *Nature*, 342 440-443 (1989).
GenBank Accession No. M73239.

*Primary Examiner*—Marianne P Allen
(74) *Attorney, Agent, or Firm*—George W. Johnston; Dennis P. Tramaloni

(57) ABSTRACT

A method for the production of the α-chain of hepatocyte growth factor or an N-terminal fragment thereof (NK polypeptide) by expression of a nucleic acid encoding said NK polypeptide in a microbial host cell, isolating inclusion bodies containing said NK polypeptide in denatured form, solubilization of the inclusion bodies and naturation of the denatured NK polypeptide, which is characterized in that in said nucleic acid at least one of the codons of amino acids selected from the group consisting of codons at positions 33, 35 and 36 is CGT, results in an improved expression yield.

7 Claims, 1 Drawing Sheet

ND STATES PATENT

METHOD FOR THE RECOMBINANT EXPRESSION OF AN N-TERMINAL FRAGMENT OF HEPATOCYTE GROWTH FACTOR

This application is the National Stage of International Application No. PCT/EP2005/002176, filed Mar. 2, 2005, which claims the benefit of European Application NO. 04004951.2, filed Mar. 3, 2004, which is hereby incorporated by reference in its entirety.

The invention relates to a method for the recombinant expression of a N-terminal four kringle-containing fragment of hepatocyte growth factor.

BACKGROUND OF THE INVENTION

Hepatocyte growth factor (HGF/SF) is a polypeptide identified and purified by Nakamura, T., et al., Biochem. Biophys. Res. Commun. 22 (1984) 1450-1459. It was further found that hepatocyte growth factor is identical to scatter factor (SF), Weidner, K. M., et al., Proc. Natl. Acad. Sci. USA 88 (1991) 7001-7005. HGF is a glycoprotein involved in the development of a number of cellular phenotypes including proliferation, mitogenesis, formation of branching tubules and, in the case of tumor cells, invasion and metastasis. For a status review, see Stuart, K. A., et al., Int. J. Exp. Pathol. 81 (2000) 17-30.

Both rat HGF and human HGF have been sequenced and cloned (Miyazawa, K. et al., Biochem. Biophys. Res. Comm. 163 (1989) 967-973; Nakamura, T., et al., Nature 342 (1989) 440-443; Seki, T., et al., Biochem. and Biophys. Res. Comm. 172 (1990) 321-327; Tashiro, K., et al., Proc. Natl. Acad. Sci. USA 87 (1990) 3200-3204; Okajima, A., et al., Eur. J. Biochem. 193 (1990) 375-381).

HGF is a protein with high similarity to human plasminogen (38% amino acid sequence identity). HGF and plasminogen are both synthesized as a single chain polypeptide which is proteolytically processed to a disulfide-linked heterodimer. HGF contains an N-terminal domain four consecutive kringle domains and a carboxyterminal, protease-like domain. Different truncated HGF variants have been described. NK1 is the shortest HGF variant described. NK1 contains amino acids 32-210 and is truncated after the first kringle domain (Lokker, N. A., and Godowski, P. J., J. Biol. Chem. 268 (1993) 17145-17150). NK2 consists of the N-terminal amino acid terminus and kringle 1 and kringle 2 and is the naturally occurring product of an alternatively spliced HGF mRNA (Chan, A. M., et al., Science 254 (1991) 1382-1385). Further HGF variants containing parts of the heavy chain of HGF (amino acids 1-494, containing the alpha-subunit of HGF from amino acids 1-463) are described by Lokker, N. A., EMBO J. 11 (1992) 2503-2510).

It was further found that an HGF/SF fragment, termed NK4, consisting of the N-terminal hairpin domain and the four kringle domains of HGF/SF has pharmacological properties that are completely different from those of HGF/SF, and is an antagonist to the influence of HGF/SF on the motility and the invasion of colon cancer cells, and is, in addition, an angiogenesis inhibitor that suppresses tumor growth and metastasis (Parr, C., et al., Int. J. Cancer 85 (2000) 563-570; Kuba, K., et al., Cancer Res. 60 (2000) 6737-6743; Date, K., et al., FEBS Lett. 420 (1997) 1-6; Date, K., et al., Oncogene 17 (1989) 3045-3054).

NK4 is prepared according to the state of the art (Date, K., et al., FEBS Lett. 420 (1997) 1-6) by recombinant expression of HGF cDNA in CHO cells and subsequent digestion with pancreatic elastase. Two other isoforms of HGF (NK1 and NK2) encoding the N-terminal domain and kringle 1, and the N-terminal domain and kringles 1 and 2, respectively, were produced in E. coli (Stahl, S. J., Biochem. J. 326 (1997) 763-772). However, this method results only in about an amount of HGF-derived proteins which is about 10-20% of the total protein.

SUMMARY OF THE INVENTION

The invention provides a method for the production of the alpha-chain of HGF or a fragment thereof (NK polypeptide) by expression of a nucleic acid encoding said NK polypeptide in a microbial host cell, isolation of inclusion bodies containing said NK polypeptide in denatured form, solubilization of the inclusion bodies and naturation of the denatured NK polypeptide, characterized in that in said nucleic acid at least one of the codons of amino acids selected from the group consisting of codons at positions 33, 35 and 36 is CGT.

Amino acid (aa) and codon numbering is according to the sequence shown in Swiss-Prot P14210, wherein aa (amino acid) 1-31 denotes signal sequence, aa 32-494 denotes alpha chain, aa 128-206 kringle 1, aa 211-288 kringle 2, aa 305-383 kringle 3 and aa391-469 kringle 4.

Surprisingly it was found, that modification of at least one of the codons of the DNA sequence of positions 33, 35 and 36 (codon 33, 35 and 36 encode arginine, numbering according to M73239) results in an increase of the expression yield of about 100% or more. It is further preferred that the codon for amino acid 32 is changed from encoding Gln to encoding Ser in order to improve splitting off N-terminal methionine.

NK polypeptides according to the invention consist of aa 32-494 or a N-terminal fragment thereof (always beginning with aa32), preferably fragment aa 32-478, the smallest fragment being aa 32-207. All NK polypeptides according to the invention show activity in a scatter assay according to Example 4.

The invention further provides a nucleic acid encoding an NK polypeptide consisting of aa 32-494 or an N-terminal fragment thereof, beginning with aa 32, preferably fragments aa 32-x, wherein x is a number between 207 and 478, and x is preferably 207 or 478, characterized in that at least one of the codons of amino acids selected from the group consisting of codons at positions 33, 35 and 36 is CGT. Preferably, all codons at positions 33, 35 and 36 are CGT.

In a preferred embodiment of the invention aa 32 is changed from glutamine to serine to improve homogeneity of the protein (cleavage of N-terminal methionine).

It is further preferred to introduce two translational stop codons (TAA, TAG and/or and TGA) at the end of the nucleic acid encoding the NK polypeptide in order to stop the translation at a position equivalent to the end of desired polypeptide.

DETAILED DESCRIPTION OF THE INVENTION

Human HGF is a disulfide-linked heterodimer, which can be cleaved in an α-subunit of 463 amino acids and a β-subunit of 234 amino acids, by cleavage between amino acids R494 and V495. The N-terminus of the α-chain is preceded by 31 amino acids started with a methionine group. This segment includes a signal sequence of 31 amino acids. The α-chain starts at amino acid 32 and contains four kringle domains. The so-called "hairpin domain" consists of amino acids 70-96. The kringle 1 domain consists of amino acids 128-206. The kringle 2 domain consists of amino acids 211-288, the kringle 3 domain consists of amino acids 305-383, and the kringle 4 domain consists of amino acids 391-469 of the α-chain, approximately. There exist variations of these sequences, essentially not affecting the biological properties of NK polypeptides (especially not affecting its activities antagonistic to HGF and its antiangiogenic activities), which variations are described, for example, in WO 93/23541. Also the length of NK polypeptides can vary within a few amino acids as long as its biological properties are not affected.

NK1 consists of aa 32 to 206-210 of the HGF/SFα-chain, NK2 consists of aa32 to 288-305 and NK4 is composed of aa 32 to 447 (resp.469-494). Further NK polypeptides encoded by the nucleic acids according to the invention and which can be produced recombinantly according to the invention are described in WO 93/23541 and are e.g. 32-207, 32-303, or 32-384. NK polypeptides have the in vivo biological activity of causing inhibition of tumor growth, angiogenesis and/or metastasis.

The NK polypeptides can be produced by recombinant means in prokaryotes. For expression in prokaryotic host cells, the nucleic acid is integrated into a suitable expression vector, according to methods familiar to a person skilled in the art. Such an expression vector preferably contains a regulatable/inducible promoter. The recombinant vector is then introduced for the expression into a suitable host cell such as, e.g., *E. coli* and the transformed cell is cultured under conditions which allow expression of the heterologous gene. After fermentation inclusion bodies containing denatured NK polypeptide are isolated.

*Escherichia, Salmonella, Streptomyces* or *Bacillus* are for example suitable as prokaryotic host organisms. For the production of NK polypeptides prokaryotes are transformed in the usual manner with the vector which contains the DNA according to the invention and encoding a NK polypeptide and subsequently fermented in the usual manner. However expression yield in *E. coli* using the original DNA sequence of a NK polypeptide (GenBank M73239) is very low.

Inclusion bodies are found in the cytoplasm as the gene to be expressed does not contain a signal sequence. These inclusion bodies are separated from other cell components, for example by centrifugation after cell lysis.

The inclusion bodies were solubilized by adding a denaturing agent like 6 M guanidinium hydrochloride or 8 M urea at pH 7-9 in phosphate buffer (preferably in a concentration of 0.1-1.0 M, e.g. 0.4 M) preferably in the presence of DTT (Dithio-1,4-threitol). The solubilisate is diluted in phosphate buffer pH 7-9 in the presence of GSH/GSSG (preferably 2-20 mM, glutahtion) and a denaturing agent in a non denaturing concentration (e.g. 2M guanidinium hydrochloride or 4 M urea) or preferably instead of guanidinium hydrochloride or urea, arginine in a concentration of about 0.3 to 1.0 M, preferably in a concentration of about 0.7M. Renaturation is performed preferably at a temperature of about 4 C and for about 48 to 160 hours.

According to the state of the art the use of Tris buffer during solubilization and naturation leads to a considerable amount (of about 50%) of side-products which are identified by the inventors as consisting mainly of GSH-modified NK polypeptides. To the contrary, it was surprisingly found that the use of potassium phosphate buffer in a pH range between 7 and 9, preferably between pH 8 and 9, leads to a considerable improvement in yield and purity of NK polypeptides.

After naturation is terminated the solution was dialyzed preferably against phosphate buffer pH 7-9 (preferably in a concentration of 0.1-1.0 M, e.g. 0.3 M) for at least 24 hours, preferably for 24-120 hours.

NK polypeptides can be purified after recombinant production and naturation of the water insoluble denatured polypeptide (inclusion bodies) according to the method of the invention preferably by chromatographic methods, e.g. by affinity chromatography, hydrophobic interaction chromatography, immunoprecipitation, gel filtration, ion exchange chromatography, chromatofocussing, isoelectric focussing, selective precipitation, electrophoresis, or the like. It is preferred to purify NK polypeptides by hydrophobic interaction chromatography, preferably at pH 7-9, in the presence of phosphate buffer and/or by the use of butyl- or phenyl sepharose.

The following examples, references, figure and sequence listing are provided to aid the understanding of the present invention, the true scope of which is set forth in the appended claims. It is understood that modifications can be made in the procedures set forth without departing from the spirit of the invention.

DESCRIPTION OF THE SEQUENCES

Figure 1:
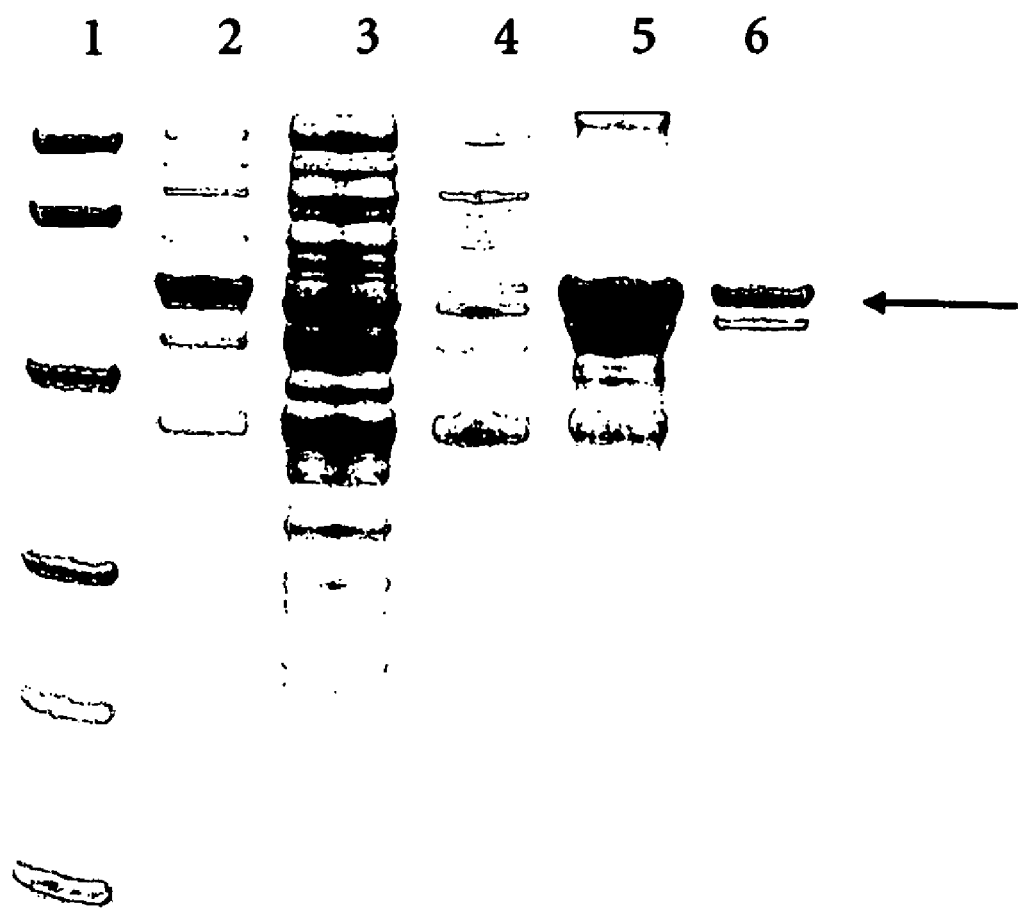
FIG. 1: SDS-Gel (10% NuPAGE-SDS, 5 µl per lane, numbering from left to right) of NK4 protein in biomass and isolated inclusion bodies (IB).
 lane 1: standard
 lane 2: biomass
 lane 3: supernant after centrifugation
 lane 4: supernant after further centrifugation
 lane 5: IB preparation
 lane 6: IB preparation after wash

SEQ ID NO:1 Amino acid sequence and DNA sequence encoding the α-chain of HGF, original sequence according to GenBank M73239 (without signal sequence)
SEQ ID NO:2 Protein sequence of the α-chain of HGF
SEQ ID NO:3 Amino acid sequence and DNA sequence encoding NK4 according to the invention (amino acid sequence including N-terminal methionine, DNA sequence including two stop codons)
SEQ ID NO:4 Protein sequence of NK4

EXAMPLE 1

Recombinant Expression of NK Polypeptides

The NK4 polypeptide consisting of amino acid position 32 to 478 of HGF was used for cloning and recombinant expression in *Escherichia coli*. The original DNA sequence used as source of DNA was described (database identifier "gb: M73239"). PCR was performed in order to amplify and concurrently modify the DNA coding for NK4 (SEQ ID NO: 1). All methods were performed under standard conditions.

In comparison to the original DNA sequence of NK4, the following modifications were introduced:
 Elimination of the eukaryotic signal peptide sequence and fusion of the ATG start codon next to amino acid position 32 of NK4
 exchange of amino acid position 32 (position 2 in SEQ ID NO:2) from Gln to Ser in order to improve homogeneity of the protein product (Met-free)
 modification of the DNA sequence of the codons of amino acids at position 33 (AGG to CGT), 35 (AGA to CGT), and 36 (AGA to CGT) in order to improve gene expression in *E. coli*.
 modification of the DNA sequence of codons at position 477 (ATA to ATC) and 478 (GTC to GTT) in order to facilitate insertion of PCR product into the vector introduction of two translational stop codons at positions 479 (TAA) and 480 (TAG), in order to stop the translation at a position equivalent to the end of NK4 protein domain.

The PCR-amplified DNA fragment was treated with restriction endonucleases NdeI and BanII and was ligated to the modified pQE vector (Qiagen) (elimination of His-tag as well as DHFR coding region), which was appropriately treated with NdeI and BanII. The elements of expression plasmid pQE-NK4-Ser (plasmid size 4447 bp) are T5 promotor/lac operator element, NK4 coding region, lambda to transcriptional termination region, rrnB T1 transcriptional termination region, ColE1 origin of replication and β-lactamase coding sequence.

The ligation reaction was used to transform *E. coli* competent cells, e.g. *E. coli* strain C600 harbouring expression helper plasmid pUBS520 (EP 0 373 365). *E. coli* colonies were isolated and were characterized with respect to restriction and sequence analysis of their plasmids. The selection of clones was done by analysis of the NK4 protein content after cultivation of recombinant cells in LB medium in the presence of appropriate antibiotics and after induction of the gene expression by addition of IPTG (1 mM). The protein pattern of cell lysates were compared by PAGE. The recombinant *E. coli* done showing the highest proportion of NK4 protein was selected for the production process. Fermentation was performed under standard conditions and inclusion bodies were isolated. Yield: 130 g/l net weight of cells with 30%-40% NK4 of total protein.

NK1 and NK2 can be produced recombinantly in an analogous manner.

EXAMPLE 2

Solubilization and Naturation

Inclusion bodies were dissolved over night in a buffer containing 6 M guanidinium hydrochloride, 0.1 M potassium phosphate pH 8.5 (by titration with 10 M KOH), 1 mM EDTA, 0.01 mM DTT. The concentration of the dissolved protein was determined by Biuret assay and finally adjusted to a concentration of 25 mg total protein/ml at room temperature.

This NK-solubilisate was diluted to a concentration of 0.4 mg/ml in a buffer containing 0.7 M arginine, 0.1 M potassium phosphate pH 8.5 (by titration with conc. HCl), 10 mM GSH, 5 mM GSSG and 1 mM EDTA. This renaturation assay was incubated between 2 and 8 days at 4° C. After obtaining the maximal renaturation efficacy, the renaturation assay of 15 l volume was concentrated to 3 l using a tangential flow filtration unit (MW cut off: 10 kDa, Sartorius). It was subsequently dialyzed against 3 times 50 l buffer containing 0.3 M potassium phosphate at pH 8.0 for at least 3×24 hours, optimally for 5 days in total.

EXAMPLE 3

Purification

Purification was performed by Heparin-Sepharose chromatography.

Buffer conditions:
Buffer A: 50 mM Tris pH 8.0
Buffer B: 50 mM Tris pH 8.0, 2 M NaCl
Gradient: 5-25% buffer B, 2 column volumes

| Gradient: | 5-25% | buffer B, 2 column volumes |
|---|---|---|
| | 25-55% | buffer B, 16 column volumes |
| | 55-100% | buffer B, 0.7 column volumes |
| | 100% | buffer B, 2 column volumes |

To the eluted material 1 M ammonium sulfate in 0.1 M potassium phosphate pH 8.0 was added and incubated at 4° C. overnight. The sample was centrifuged and the supernatant was loaded on a Phenyl Sepharose column (150 ml). The column was washed with 1 column volume 1 M ammonium sulfate, 50 mM potassium phosphate pH 8.0.

Elution conditions:
Buffer A: 1 M ammonium sulfate, 50 mM potassium phosphate pH 8.0
Buffer B: 50 mM potassium phosphate pH 8.0, 40% ethylene glycol 0-100% buffer B, 20 column volumes

EXAMPLE 4

Determination of Activity a) Scatter Assay

MDCK cells were subconfluently grown in tissue culture plates. Cells were treated with HGF (10 ng/ml) or with combinations of HGF and NK4. In these experiments the HGF-induced cell scattering was inhibited by the addition of a 10 to 1000-fold molar excess of NK4 at least for 90% and more, showing the functional activity.

b) Proliferation Assay

Inhibition of the mitogenic activity of HGF by NK4 was determined by measuring DNA synthesis of adult rat hepatocytes in primary culture as described in Nakamura et al. (1989). In these experiments the HGF-induced cell proliferation was inhibited by the addition of a 10 to 1000-fold molar excess of NK4 at least for 90% and more, showing the functional activity.

c) Invasion Assay

In this assay the invasive potential of tumor cells is analyzed. The assay was done essentially as described in Albini, A., et al., Cancer Res. 47 (1987) 3239-3245, using HT115 cells. Again, HGF-induced (10 ng/ml) cell invasion could be inhibited by a 10 to 1000-fold molar excess of NK4 at least for 90% and more, showing the functional activity.

EXAMPLE 5

Activity in vivo

Model: Lewis Lung Carcinoma nude mouse tumor model
  1×10$^6$ Lewis Lung Carcinoma cells were s.c. implanted into male nude mice (BALB/c nu/nu).
Treatment: After 4 days, one application daily of pegylated NK4 over a period of 2-4 weeks
Dose: 1000 µg/mouse/day
  300 µg/mouse/day
  100 µg/mouse/day
  placebo
Result: Treatment with NK4 shows a dose dependent suppression of primary tumor growth and metastasis, whereas no effect is seen in placebo treated groups.

LIST OF REFERENCES

Albini, A., et al., Cancer Res. 47 (1987) 3239-3245
Chan, A. M., et al., Science 254 (1991) 1382-1385

Date, K., et al., FEBS Lett. 420 (1997) 1-6
Date, K., et al., Oncogene 17 (1989) 3045-3054
EP 0 373 365
Kuba, K., et al., Cancer Res. 60 (2000) 6737-6743
Lokker, N. A., and Godowski, P. J., J. Biol. Chem. 268 (1993) 17145-17150
Lokker, N. A., EMBO J. 11 (1992) 2503-2510
Miyazawa, K. et al., Biochem. Biophys. Res. Comm. 163 (1989) 967-973
Nakamura, T., et al., Biochem. Biophys. Res. Commun. 22 (1984) 1450-1459
Nakamura, T., et al., Nature 342 (1989) 440-443
Okajima, A., et al., Eur. J. Biochem. 193 (1990) 375-381
Parr, C., et al., Int. J. Cancer 85 (2000) 563-570
Seki, T., et al., Biochem. and Biophys. Res. Comm. 172 (1990) 321-327
Stahl, S. J., Biochem. J. 326 (1997) 763-772
Stuart, K. A., et al., Int. J. Exp. Pathol. 81 (2000) 17-30
Tashiro, K., et al., Proc. Natl. Acad. Sci. USA 87 (1990) 3200-3204
Weidner, K. M., et al., Proc. Natl. Acad. Sci. USA 88 (1991) 7001-7005
WO 93/23541

The invention claimed is:

1. A nucleic acid comprising nucleotides 1-531 of SEQ ID NO:3.

2. A nucleic acid comprising nucleotides 1-1344 of SEQ ID NO:3.

3. A nucleic acid encoding amino acids 1-177 of SEQ ID NO:4 wherein at least one of the codons encoding Arg at amino acid positions 3, 5 and 6 of SEQ ID NO:4 is CGT.

4. The nucleic acid of claim 3 wherein each of the codons encoding Arg at amino acid positions 3, 5 and 6 of SEQ ID NO:4 is CGT.

5. A nucleic acid encoding SEQ ID NO:4 wherein at least one of the codons encoding Arg at amino acid positions 3, 5 and 6 of SEQ ID NO:4 is CGT.

6. The nucleic acid of claim 5 wherein each of the codons encoding Arg at amino acid positions 3, 5 and 6 of SEQ ID NO:4 is CGT.

7. A method for the production of an NK polypeptide comprising the α-chain of hepatocyte growth factor polypeptide or an N-terminal fragment thereof comprising the steps of
a) expressing the nucleic acid of any one of claims 1-6 in a microbial host cell;
b) isolating inclusion bodies containing said NK polypeptide in denatured form;
c) solubilizing the inclusion bodies; and
d) renaturing the denatured NK polypeptide.

* * * * *

SEQUENCE LISTING

```
<160> NUMBER OF SEQ ID NOS: 4

<210> SEQ ID NO 1
<211> LENGTH: 1389
<212> TYPE: DNA
<213> ORGANISM: Homo sapiens
<220> FEATURE:
<221> NAME/KEY: CDS
<222> LOCATION: (1)..(1389)
<223> OTHER INFORMATION: DNA sequence encoding the alpha-chain of
      hepatocyte growth factor (HGF)

<400> SEQUENCE: 1 caa agg aaa aga aga aat aca att cat gaa ttc aaa aaa tca gca aag      48
Gln Arg Lys Arg Arg Asn Thr Ile His Glu Phe Lys Lys Ser Ala Lys
1               5                   10                  15 act acc cta atc aaa ata gat cca gca ctg aag ata aaa acc aaa aaa      96
Thr Thr Leu Ile Lys Ile Asp Pro Ala Leu Lys Ile Lys Thr Lys Lys
                20                  25                  30 gtg aat act gca gac caa tgt gct aat aga tgt act agg aat aaa gga    144
Val Asn Thr Ala Asp Gln Cys Ala Asn Arg Cys Thr Arg Asn Lys Gly
            35                  40                  45 ctt cca ttc act tgc aag gct ttt gtt ttt gat aaa gca aga aaa caa    192
Leu Pro Phe Thr Cys Lys Ala Phe Val Phe Asp Lys Ala Arg Lys Gln
        50                  55                  60 tgc ctc tgg ttc ccc ttc aat agc atg tca agt gga gtg aaa aaa gaa    240
Cys Leu Trp Phe Pro Phe Asn Ser Met Ser Ser Gly Val Lys Lys Glu
65                  70                  75                  80 ttt ggc cat gaa ttt gac ctc tat gaa aac aaa gac tac att aga aac    288
Phe Gly His Glu Phe Asp Leu Tyr Glu Asn Lys Asp Tyr Ile Arg Asn
                85                  90                  95 tgc atc att ggt aaa gga cgc agc tac aag gga aca gta tct atc act    336
Cys Ile Ile Gly Lys Gly Arg Ser Tyr Lys Gly Thr Val Ser Ile Thr
                100                 105                 110 aag agt ggc atc aaa tgt cag ccc tgg agt tcc atg ata cca cac gaa    384
Lys Ser Gly Ile Lys Cys Gln Pro Trp Ser Ser Met Ile Pro His Glu
            115                 120                 125 cac agc ttt ttg cct tcg agc tat cgg ggt aaa gac cta cag gaa aac    432
His Ser Phe Leu Pro Ser Ser Tyr Arg Gly Lys Asp Leu Gln Glu Asn
        130                 135                 140 tac tgt cga aat cct cga ggg gaa gaa ggg gga ccc tgg tgt ttc aca    480
Tyr Cys Arg Asn Pro Arg Gly Glu Glu Gly Gly Pro Trp Cys Phe Thr
145                 150                 155                 160 agc aat cca gag gta cgc tac gaa gtc tgt gac att cct cag tgt tca    528
Ser Asn Pro Glu Val Arg Tyr Glu Val Cys Asp Ile Pro Gln Cys Ser
                165                 170                 175 gaa gtt gaa tgc atg acc tgc aat ggg gag agt tat cga ggt ctc atg    576
Glu Val Glu Cys Met Thr Cys Asn Gly Glu Ser Tyr Arg Gly Leu Met
```

|  |  |  |  |  |  |  |  |  |  |  |  |  |  |  |  |
|---|---|---|---|---|---|---|---|---|---|---|---|---|---|---|---|
|  |  |  | 180 |  |  |  |  | 185 |  |  |  |  | 190 |  |  |

```
gat cat aca gaa tca ggc aag att tgt cag cgc tgg gat cat cag aca      624
Asp His Thr Glu Ser Gly Lys Ile Cys Gln Arg Trp Asp His Gln Thr
        195                 200                 205 cca cac cgg cac aaa ttc ttg cct gaa aga tat ccc gac aag ggc ttt      672
Pro His Arg His Lys Phe Leu Pro Glu Arg Tyr Pro Asp Lys Gly Phe
210                 215                 220 gat gat aat tat tgc cgc aat ccc gat ggc cag ccg agg cca tgg tgc      720
Asp Asp Asn Tyr Cys Arg Asn Pro Asp Gly Gln Pro Arg Pro Trp Cys
225                 230                 235                 240 tat act ctt gac cct cac acc cgc tgg gag tac tgt gca att aaa aca      768
Tyr Thr Leu Asp Pro His Thr Arg Trp Glu Tyr Cys Ala Ile Lys Thr
            245                 250                 255 tgc gct gac aat act atg aat gac act gat gtt cct ttg gaa aca act      816
Cys Ala Asp Asn Thr Met Asn Asp Thr Asp Val Pro Leu Glu Thr Thr
        260                 265                 270 gaa tgc atc caa ggt caa gga gaa ggc tac agg ggc act gtc aat acc      864
Glu Cys Ile Gln Gly Gln Gly Glu Gly Tyr Arg Gly Thr Val Asn Thr
    275                 280                 285 att tgg aat gga att cca tgt cag cgt tgg gat tct cag tat cct cac      912
Ile Trp Asn Gly Ile Pro Cys Gln Arg Trp Asp Ser Gln Tyr Pro His
290                 295                 300 gag cat gac atg act cct gaa aat ttc aag tgc aag gac cta cga gaa      960
Glu His Asp Met Thr Pro Glu Asn Phe Lys Cys Lys Asp Leu Arg Glu
305                 310                 315                 320 aat tac tgc cga aat cca gat ggg tct gaa tca ccc tgg tgt ttt acc     1008
Asn Tyr Cys Arg Asn Pro Asp Gly Ser Glu Ser Pro Trp Cys Phe Thr
            325                 330                 335 act gat cca aac atc cga gtt ggc tac tgc tcc caa att cca aac tgt     1056
Thr Asp Pro Asn Ile Arg Val Gly Tyr Cys Ser Gln Ile Pro Asn Cys
        340                 345                 350 gat atg tca cat gga caa gat tgt tat cgt ggg aat ggc aaa aat tat     1104
Asp Met Ser His Gly Gln Asp Cys Tyr Arg Gly Asn Gly Lys Asn Tyr
    355                 360                 365 atg ggc aac tta tcc caa aca aga tct gga cta aca tgt tca atg tgg     1152
Met Gly Asn Leu Ser Gln Thr Arg Ser Gly Leu Thr Cys Ser Met Trp
370                 375                 380 gac aag aac atg gaa gac tta cat cgt cat atc ttc tgg gaa cca gat     1200
Asp Lys Asn Met Glu Asp Leu His Arg His Ile Phe Trp Glu Pro Asp
385                 390                 395                 400 gca agt aag ctg aat gag aat tac tgc cga aat cca gat gat gat gct     1248
Ala Ser Lys Leu Asn Glu Asn Tyr Cys Arg Asn Pro Asp Asp Asp Ala
            405                 410                 415 cat gga ccc tgg tgc tac acg gga aat cca ctc att cct tgg gat tat     1296
His Gly Pro Trp Cys Tyr Thr Gly Asn Pro Leu Ile Pro Trp Asp Tyr
        420                 425                 430 tgc cct att tct cgt tgt gaa ggt gat acc aca cct aca ata gtc aat     1344
Cys Pro Ile Ser Arg Cys Glu Gly Asp Thr Thr Pro Thr Ile Val Asn
    435                 440                 445 tta gac cat ccc gta ata tct tgt gcc aaa acg aaa caa ttg cga         1389
Leu Asp His Pro Val Ile Ser Cys Ala Lys Thr Lys Gln Leu Arg
450                 455                 460
```

<210> SEQ ID NO 2
<211> LENGTH: 463
<212> TYPE: PRT
<213> ORGANISM: Homo sapiens

<400> SEQUENCE: 2

Gln Arg Lys Arg Arg Asn Thr Ile His Glu Phe Lys Lys Ser Ala Lys

-continued

```
1               5              10              15

Thr Thr Leu Ile Lys Ile Asp Pro Ala Leu Lys Ile Thr Lys Lys
                20              25              30

Val Asn Thr Ala Asp Gln Cys Ala Asn Arg Cys Thr Arg Asn Lys Gly
                35              40              45

Leu Pro Phe Thr Cys Lys Ala Phe Val Phe Asp Lys Ala Arg Lys Gln
50                              55              60

Cys Leu Trp Phe Pro Phe Asn Ser Met Ser Ser Gly Val Lys Lys Glu
65                      70              75                      80

Phe Gly His Glu Phe Asp Leu Tyr Glu Asn Lys Asp Tyr Ile Arg Asn
                        85              90              95

Cys Ile Ile Gly Lys Gly Arg Ser Tyr Lys Gly Thr Val Ser Ile Thr
                100             105             110

Lys Ser Gly Ile Lys Cys Gln Pro Trp Ser Ser Met Ile Pro His Glu
                115             120             125

His Ser Phe Leu Pro Ser Ser Tyr Arg Gly Lys Asp Leu Gln Glu Asn
                130             135             140

Tyr Cys Arg Asn Pro Arg Gly Glu Glu Gly Gly Pro Trp Cys Phe Thr
145                     150             155                     160

Ser Asn Pro Glu Val Arg Tyr Glu Val Cys Asp Ile Pro Gln Cys Ser
                        165             170             175

Glu Val Glu Cys Met Thr Cys Asn Gly Glu Ser Tyr Arg Gly Leu Met
                180             185             190

Asp His Thr Glu Ser Gly Lys Ile Cys Gln Arg Trp Asp His Gln Thr
                195             200             205

Pro His Arg His Lys Phe Leu Pro Glu Arg Tyr Pro Asp Lys Gly Phe
                210             215             220

Asp Asp Asn Tyr Cys Arg Asn Pro Asp Gly Gln Pro Arg Pro Trp Cys
225                     230             235                     240

Tyr Thr Leu Asp Pro His Thr Arg Trp Glu Tyr Cys Ala Ile Lys Thr
                        245             250             255

Cys Ala Asp Asn Thr Met Asn Asp Thr Asp Val Pro Leu Glu Thr Thr
                260             265             270

Glu Cys Ile Gln Gly Gln Gly Glu Gly Tyr Arg Gly Thr Val Asn Thr
                275             280             285

Ile Trp Asn Gly Ile Pro Cys Gln Arg Trp Asp Ser Gln Tyr Pro His
                290             295             300

Glu His Asp Met Thr Pro Glu Asn Phe Lys Cys Lys Asp Leu Arg Glu
305                     310             315                     320

Asn Tyr Cys Arg Asn Pro Asp Gly Ser Glu Ser Pro Trp Cys Phe Thr
                        325             330             335

Thr Asp Pro Asn Ile Arg Val Gly Tyr Cys Ser Gln Ile Pro Asn Cys
                340             345             350

Asp Met Ser His Gly Gln Asp Cys Tyr Arg Gly Asn Gly Lys Asn Tyr
                355             360             365

Met Gly Asn Leu Ser Gln Thr Arg Ser Gly Leu Thr Cys Ser Met Trp
                370             375             380

Asp Lys Asn Met Glu Asp Leu His Arg His Ile Phe Trp Glu Pro Asp
385                     390             395                     400

Ala Ser Lys Leu Asn Glu Asn Tyr Cys Arg Asn Pro Asp Asp Asp Ala
                        405             410             415

His Gly Pro Trp Cys Tyr Thr Gly Asn Pro Leu Ile Pro Trp Asp Tyr
                420             425             430
```

```
Cys Pro Ile Ser Arg Cys Glu Gly Asp Thr Thr Pro Thr Ile Val Asn
        435                 440                 445

Leu Asp His Pro Val Ile Ser Cys Ala Lys Thr Lys Gln Leu Arg
        450                 455                 460

<210> SEQ ID NO 3
<211> LENGTH: 1350
<212> TYPE: DNA
<213> ORGANISM: Artificial
<220> FEATURE:
<223> OTHER INFORMATION: dna coding for NK4
<220> FEATURE:
<221> NAME/KEY: CDS
<222> LOCATION: (1)..(1350)

<400> SEQUENCE: 3 atg tct cgt aaa cgt cgt aat act att cat gaa ttc aaa aaa tca gca       48
Met Ser Arg Lys Arg Arg Asn Thr Ile His Glu Phe Lys Lys Ser Ala
1               5                   10                  15 aag act acc cta atc aaa ata gat cca gca ctg aag ata aaa acc aaa       96
Lys Thr Thr Leu Ile Lys Ile Asp Pro Ala Leu Lys Ile Lys Thr Lys
            20                  25                  30 aaa gtg aat act gca gac caa tgt gct aat aga tgt act agg aat aaa      144
Lys Val Asn Thr Ala Asp Gln Cys Ala Asn Arg Cys Thr Arg Asn Lys
        35                  40                  45 gga ctt cca ttc act tgc aag gct ttt gtt ttt gat aaa gca aga aaa      192
Gly Leu Pro Phe Thr Cys Lys Ala Phe Val Phe Asp Lys Ala Arg Lys
    50                  55                  60 caa tgc ctc tgg ttc ccc ttc aat agc atg tca agt gga gtg aaa aaa      240
Gln Cys Leu Trp Phe Pro Phe Asn Ser Met Ser Ser Gly Val Lys Lys
65                  70                  75                  80 gaa ttt ggc cat gaa ttt gac ctc tat gaa aac aaa gac tac att aga      288
Glu Phe Gly His Glu Phe Asp Leu Tyr Glu Asn Lys Asp Tyr Ile Arg
                85                  90                  95 aac tgc atc att ggt aaa gga cgc agc tac aag gga aca gta tct atc      336
Asn Cys Ile Ile Gly Lys Gly Arg Ser Tyr Lys Gly Thr Val Ser Ile
            100                 105                 110 act aag agt ggc atc aaa tgt cag ccc tgg agt tcc atg ata cca cac      384
Thr Lys Ser Gly Ile Lys Cys Gln Pro Trp Ser Ser Met Ile Pro His
        115                 120                 125 gaa cac agc ttt ttg cct tcg agc tat cgg ggt aaa gac cta cag gaa      432
Glu His Ser Phe Leu Pro Ser Ser Tyr Arg Gly Lys Asp Leu Gln Glu
    130                 135                 140 aac tac tgt cga aat cct cga ggg gaa gaa ggg gga ccc tgg tgt ttc      480
Asn Tyr Cys Arg Asn Pro Arg Gly Glu Glu Gly Gly Pro Trp Cys Phe
145                 150                 155                 160 aca agc aat cca gag gta cgc tac gaa gtc tgt gac att cct cag tgt      528
Thr Ser Asn Pro Glu Val Arg Tyr Glu Val Cys Asp Ile Pro Gln Cys
                165                 170                 175 tca gaa gtt gaa tgc atg acc tgc aat ggg gag agt tat cga ggt ctc      576
Ser Glu Val Glu Cys Met Thr Cys Asn Gly Glu Ser Tyr Arg Gly Leu
            180                 185                 190 atg gat cat aca gaa tca ggc aag att tgt cag cgc tgg gat cat cag      624
Met Asp His Thr Glu Ser Gly Lys Ile Cys Gln Arg Trp Asp His Gln
        195                 200                 205 aca cca cac cgg cac aaa ttc ttg cct gaa aga tat ccc gac aag ggc      672
Thr Pro His Arg His Lys Phe Leu Pro Glu Arg Tyr Pro Asp Lys Gly
    210                 215                 220 ttt gat gat aat tat tgc cgc aat ccc gat ggc cag ccg agg cca tgg      720
Phe Asp Asp Asn Tyr Cys Arg Asn Pro Asp Gly Gln Pro Arg Pro Trp
225                 230                 235                 240
```

```
tgc tat act ctt gac cct cac acc cgc tgg gag tac tgt gca att aaa      768
Cys Tyr Thr Leu Asp Pro His Thr Arg Trp Glu Tyr Cys Ala Ile Lys
            245                 250                 255 aca tgc gct gac aat act atg aat gac act gat gtt cct ttg gaa aca      816
Thr Cys Ala Asp Asn Thr Met Asn Asp Thr Asp Val Pro Leu Glu Thr
        260                 265                 270 act gaa tgc atc caa ggt caa gga gaa ggc tac agg ggc act gtc aat      864
Thr Glu Cys Ile Gln Gly Gln Gly Glu Gly Tyr Arg Gly Thr Val Asn
    275                 280                 285 acc att tgg aat gga att cca tgt cag cgt tgg gat tct cag tat cct      912
Thr Ile Trp Asn Gly Ile Pro Cys Gln Arg Trp Asp Ser Gln Tyr Pro
290                 295                 300 cac gag cat gac atg act cct gaa aat ttc aag tgc aag gac cta cga      960
His Glu His Asp Met Thr Pro Glu Asn Phe Lys Cys Lys Asp Leu Arg
305                 310                 315                 320 gaa aat tac tgc cga aat cca gat ggg tct gaa tca ccc tgg tgt ttt     1008
Glu Asn Tyr Cys Arg Asn Pro Asp Gly Ser Glu Ser Pro Trp Cys Phe
                325                 330                 335 acc act gat cca aac atc cga gtt ggc tac tgc tcc caa att cca aac     1056
Thr Thr Asp Pro Asn Ile Arg Val Gly Tyr Cys Ser Gln Ile Pro Asn
            340                 345                 350 tgt gat atg tca cat gga caa gat tgt tat cgt ggg aat ggc aaa aat     1104
Cys Asp Met Ser His Gly Gln Asp Cys Tyr Arg Gly Asn Gly Lys Asn
        355                 360                 365 tat atg ggc aac tta tcc caa aca aga tct gga cta aca tgt tca atg     1152
Tyr Met Gly Asn Leu Ser Gln Thr Arg Ser Gly Leu Thr Cys Ser Met
    370                 375                 380 tgg gac aag aac atg gaa gac tta cat cgt cat atc ttc tgg gaa cca     1200
Trp Asp Lys Asn Met Glu Asp Leu His Arg His Ile Phe Trp Glu Pro
385                 390                 395                 400 gat gca agt aag ctg aat gag aat tac tgc cga aat cca gat gat gat     1248
Asp Ala Ser Lys Leu Asn Glu Asn Tyr Cys Arg Asn Pro Asp Asp Asp
                405                 410                 415 gct cat gga ccc tgg tgc tac acg gga aat cca ctc att cct tgg gat     1296
Ala His Gly Pro Trp Cys Tyr Thr Gly Asn Pro Leu Ile Pro Trp Asp
            420                 425                 430 tat tgc cct att tct cgt tgt gaa ggt gat acc aca cct aca atc gtt     1344
Tyr Cys Pro Ile Ser Arg Cys Glu Gly Asp Thr Thr Pro Thr Ile Val
        435                 440                 445 taa tag                                                             1350

<210> SEQ ID NO 4
<211> LENGTH: 448
<212> TYPE: PRT
<213> ORGANISM: Artificial
<220> FEATURE:
<223> OTHER INFORMATION: protein sequence of NK4

<400> SEQUENCE: 4

Met Ser Arg Lys Arg Asn Thr Ile His Glu Phe Lys Lys Ser Ala
1               5                   10                  15

Lys Thr Thr Leu Ile Lys Ile Asp Pro Ala Leu Lys Ile Lys Thr Lys
            20                  25                  30

Lys Val Asn Thr Ala Asp Gln Cys Ala Asn Arg Cys Thr Arg Asn Lys
        35                  40                  45

Gly Leu Pro Phe Thr Cys Lys Ala Phe Val Phe Asp Lys Ala Arg Lys
    50                  55                  60

Gln Cys Leu Trp Phe Pro Phe Asn Ser Met Ser Ser Gly Val Lys Lys
65                  70                  75                  80
```

-continued

```
Glu Phe Gly His Glu Phe Asp Leu Tyr Glu Asn Lys Asp Tyr Ile Arg
                85                  90                  95

Asn Cys Ile Ile Gly Lys Gly Arg Ser Tyr Lys Gly Thr Val Ser Ile
            100                 105                 110

Thr Lys Ser Gly Ile Lys Cys Gln Pro Trp Ser Ser Met Ile Pro His
        115                 120                 125

Glu His Ser Phe Leu Pro Ser Ser Tyr Arg Gly Lys Asp Leu Gln Glu
    130                 135                 140

Asn Tyr Cys Arg Asn Pro Arg Gly Glu Glu Gly Gly Pro Trp Cys Phe
145                 150                 155                 160

Thr Ser Asn Pro Glu Val Arg Tyr Glu Val Cys Asp Ile Pro Gln Cys
                165                 170                 175

Ser Glu Val Glu Cys Met Thr Cys Asn Gly Glu Ser Tyr Arg Gly Leu
            180                 185                 190

Met Asp His Thr Glu Ser Gly Lys Ile Cys Gln Arg Trp Asp His Gln
        195                 200                 205

Thr Pro His Arg His Lys Phe Leu Pro Glu Arg Tyr Pro Asp Lys Gly
    210                 215                 220

Phe Asp Asp Asn Tyr Cys Arg Asn Pro Asp Gly Gln Pro Arg Pro Trp
225                 230                 235                 240

Cys Tyr Thr Leu Asp Pro His Thr Arg Trp Glu Tyr Cys Ala Ile Lys
                245                 250                 255

Thr Cys Ala Asp Asn Thr Met Asn Asp Thr Asp Val Pro Leu Glu Thr
            260                 265                 270

Thr Glu Cys Ile Gln Gly Gln Gly Glu Gly Tyr Arg Gly Thr Val Asn
        275                 280                 285

Thr Ile Trp Asn Gly Ile Pro Cys Gln Arg Trp Asp Ser Gln Tyr Pro
    290                 295                 300

His Glu His Asp Met Thr Pro Glu Asn Phe Lys Cys Lys Asp Leu Arg
305                 310                 315                 320

Glu Asn Tyr Cys Arg Asn Pro Asp Gly Ser Glu Ser Pro Trp Cys Phe
                325                 330                 335

Thr Thr Asp Pro Asn Ile Arg Val Gly Tyr Cys Ser Gln Ile Pro Asn
            340                 345                 350

Cys Asp Met Ser His Gly Gln Asp Cys Tyr Arg Gly Asn Gly Lys Asn
        355                 360                 365

Tyr Met Gly Asn Leu Ser Gln Thr Arg Ser Gly Leu Thr Cys Ser Met
    370                 375                 380

Trp Asp Lys Asn Met Glu Asp Leu His Arg His Ile Phe Trp Glu Pro
385                 390                 395                 400

Asp Ala Ser Lys Leu Asn Glu Asn Tyr Cys Arg Asn Pro Asp Asp Asp
                405                 410                 415

Ala His Gly Pro Trp Cys Tyr Thr Gly Asn Pro Leu Ile Pro Trp Asp
            420                 425                 430

Tyr Cys Pro Ile Ser Arg Cys Glu Gly Asp Thr Thr Pro Thr Ile Val
        435                 440                 445
```